United States Patent
Yoshikawa et al.

(10) Patent No.: US 6,311,543 B1
(45) Date of Patent: Nov. 6, 2001

(54) CONNECTION DEVICE FOR CERAMIC GAS SENSOR ELEMENT

(75) Inventors: Takaya Yoshikawa; Katsuhisa Yabuta; Masaya Ito; Hisaharu Nishio, all of Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/306,376

(22) Filed: May 6, 1999

Related U.S. Application Data

(60) Provisional application No. 60/129,031, filed on Apr. 13, 1999.

(30) Foreign Application Priority Data

May 8, 1998 (JP) .................................................. 10-125859

(51) Int. Cl.[7] .................................................. G01N 27/12
(52) U.S. Cl. ........................... 73/23.2; 73/23.31; 73/31.05
(58) Field of Search ................................... 73/23.2, 23.31, 73/31.05; 204/426

(56) References Cited

U.S. PATENT DOCUMENTS

| | | | |
|---|---|---|---|
| 4,596,132 | * | 6/1986 | Takami et al. ........................ 73/31.05 |
| 4,983,271 | | 1/1991 | Kato ....................................... 204/426 |
| 5,329,806 | * | 7/1994 | McClanahan et al. .............. 73/31.05 |

FOREIGN PATENT DOCUMENTS

| | | |
|---|---|---|
| 196 38 208 | 4/1998 | (DE) . |
| 0 624 790 | 11/1994 | (EP) . |
| 0 836 094 A2 | 4/1998 | (EP) .................................... 73/31.05 |
| 10-253568 | 9/1998 | (JP) ..................................... 73/31.05 |
| 10-253579 | 9/1998 | (JP) ..................................... 73/31.05 |
| WO 92/08127 | 5/1992 | (WO) . |

* cited by examiner

*Primary Examiner*—Daniel S. Larkin
(74) *Attorney, Agent, or Firm*—Morgan, Lewis & Bockius LLP

(57) ABSTRACT

A connection device for a ceramic gas sensor element includes a sensor assembly and a ring member. The sensor assembly has a ceramic element with a thickness t, an electrical connection portion formed on a side of the ceramic element, and at least one electrical lead in contact with the electrical connection portion, wherein the sensor assembly defines an outer dimension at a position corresponding to the electrical connection portion. The ring member is disposed around the sensor assembly to hold the at least one electrical lead in contact with the electrical connection portion such that the ring member has an inner dimension at a position corresponding to the connection portion that is smaller than the outer dimension of the sensor element. The ring member defines an axial length L that contacts the sensor assembly such that the thickness t and the axial length L satisfy the relation $0.23 \leq L/t \leq 13$.

20 Claims, 8 Drawing Sheets

CONNECTION DEVICE FOR CERAMIC GAS SENSOR ELEMENT

This application claims the benefit of Japanese Patent Application No. Hei. 10-125859, filed in Japan on May 8, 1998, and U.S. Provisional Patent Application No. 60/129, 031, entitled "Connection Device for Ceramic Element" by Yoshikawa et al., filed in the United States on Apr. 13, 1999, which are hereby incorporated by reference.

BACKGROUND OF THE INVENTION

1. Field of the Invention

The present invention relates to a gas sensor, and more particularly, to a connection device for providing a heat-resistant joint between a ceramic element and lead strips.

2. Discussion of the Related Art

Oxygen sensor elements are known in the art to be made from ceramic elements. Commonly, ceramic elements are used in vehicles to determine the oxygen concentration of exhaust gases. Because the ceramic element is attached to an exhaust pipe, it will be exposed to high temperatures. FIG. 10 shows a configuration of the type disclosed in Japanese Laid-Open Patent Publication No. 10-253579 and Published European Patent Application No. EP 836094 (the disclosures of which are hereby incorporated by reference) having improved heat stability in an oxygen sensor element with a ceramic element.

As shown in FIG. 10, a ceramic element 30 to be attached to an exhaust pipe (not shown) is electrically connected to lead strips 38 by fitting a metallic ring 31 thereto with an insulation sheet 39 being disposed between the metallic ring 31 and the lead strips 38. Here, the metallic ring 31 is provided to have an appropriate interference amount and an appropriate minimum wall thickness.

Size reduction of the sensor is accompanied by reduction in the distance between an attachment portion of the sensor to an exhaust pipe and a connection portion between the ceramic element 30 and lead strip 38. Consequently, the connection portion is exposed to even higher temperatures.

The ceramic element 30 has been found to be strong with respect to compressive stresses, but weak with respect to tensile stresses. When the electrodes of lead strip 38 and the ceramic element 30 are joined through interference fitting, compressive stresses act on the joint portion of the ceramic element 30, which poses no problem. However, when the sensor is used at high temperatures, the joint portion undergoes thermal fatigue, thereby causing differences in thermal expansion among the elements of the sensor. The differences in thermal expansion result in the formation of cracks x, as shown in FIG. 10. In the worst case, a malfunction of the ceramic element 30 will result. When the interference amount is decreased in order to avoid the crack problem, a retaining force for the electrodes of the lead strips 38 decreases, thereby failing to reliably join the electrodes and the ceramic element 30.

SUMMARY OF THE INVENTION

Accordingly, the present invention is directed to a connection device for a ceramic element that substantially obviates one or more of the problems encountered in the related art devices.

An object of the present invention is to provide a connection device for a ceramic element for strongly and reliably joining lead strips to a ceramic element in a configuration that prevents the formation of cracks in the ceramic element even in high temperature applications.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the connection device for a ceramic gas sensor element comprises a sensor assembly including a ceramic element having a thickness t, an electrical connection portion formed on a side of the ceramic element, and at least one electrical lead in contact with the electrical connection portion. The sensor assembly defines an outer dimension at a position corresponding to the electrical connection portion. A ring member for holding the at least one electrical lead in contact with the electrical connection portion is disposed around the sensor assembly with the ring member having an inner dimension at a position corresponding to the electrical connection portion that is smaller than the outer dimension of the sensor assembly. The ring member has an axial length L in contact with the sensor assembly, wherein the thickness t and the axial length L satisfy the relationship $0.23 \leq L/t \leq 13$.

In another aspect, the connection device for a ceramic gas sensor element comprises an assembled body including a ceramic element having an electrical connection portion and lead strips in contact with the electrical connection portion and extending outward; and a ring member having an inner dimension smaller than an outer dimension of the assembled body, the ring member being interference-fitted onto the assembled body to thereby mechanically press the lead strips against the electrical connection portion of the ceramic element, wherein a thickness t of the ceramic element and an axial length L of a portion of the ring member in contact with the assembled body satisfy the relationship $0.23 \leq L/t \leq 13$.

In a further aspect, the connection device for a ceramic gas sensor element comprises a ceramic element having a thickness t; an electrical connection portion formed on a side of the ceramic element; an electrical lead in contact with the electrical connection portion; an insulating layer disposed on the electrical lead; a ring member disposed around the ceramic element, the electrical connection portion, the electrical lead, and the insulating layer, the ring member for holding the electrical lead in contact with the electrical connection portion, wherein the ring member has an inner dimension that is smaller than an outer dimension defined by the ceramic element, the electrical connection portion, the electrical lead, and the insulating layer, and wherein the ring member has an axial length L in contact with the insulating layer such that the thickness t and the axial length L satisfy the relationship $0.23 \leq L/t \leq 13$.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1A:
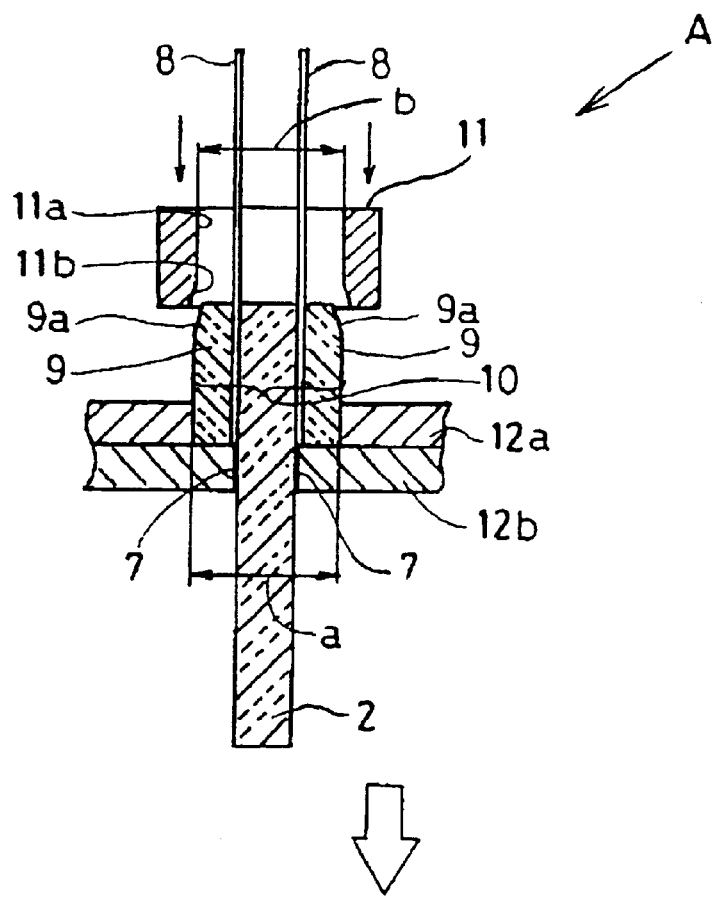
FIGS. 1A–1B are sectional views showing a procedure for assembling a connection device for a ceramic element.
Figure 1B:
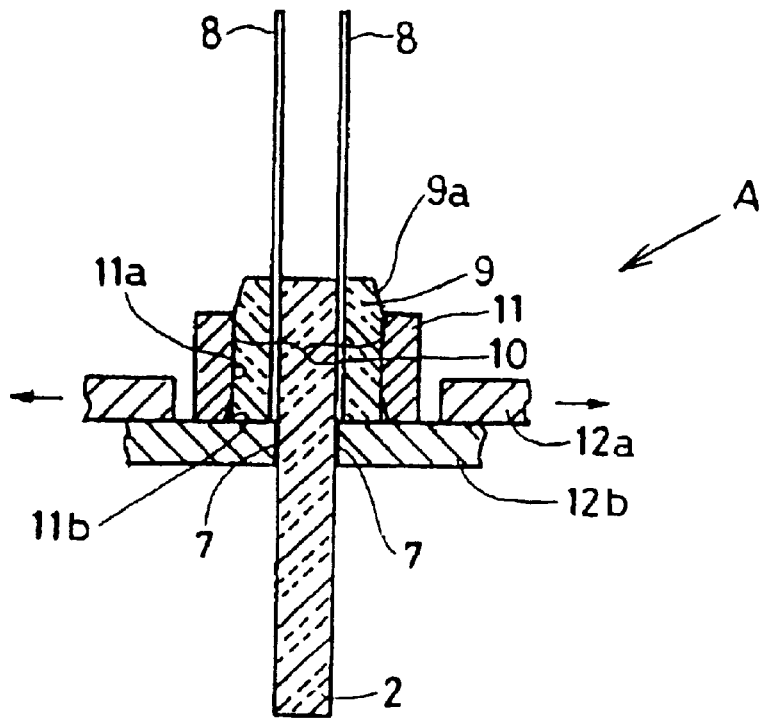
Figure 2:
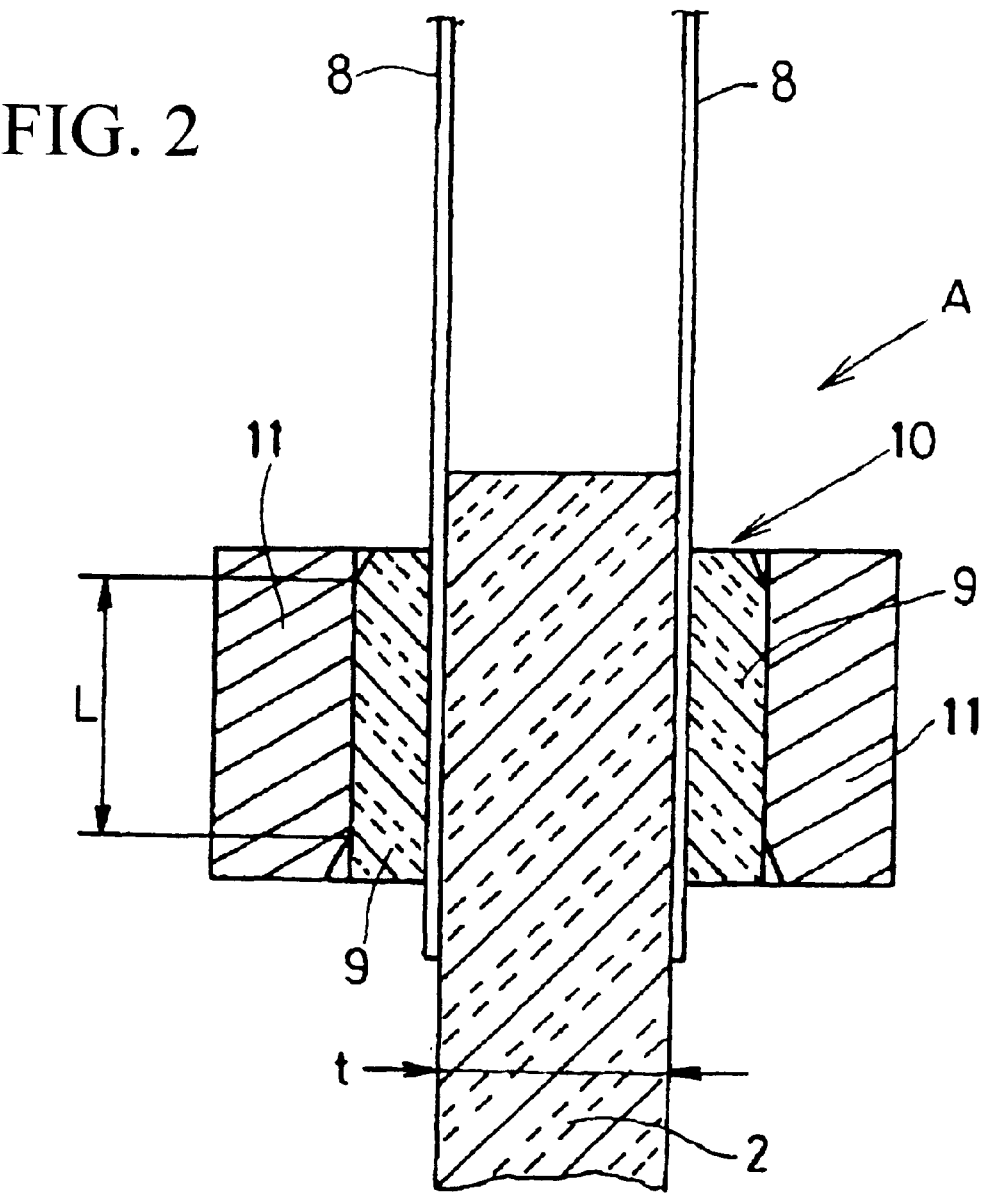
FIG. 2 is an enlarged sectional view showing related portions of the connection device of FIG. 1B.
Figure 3:
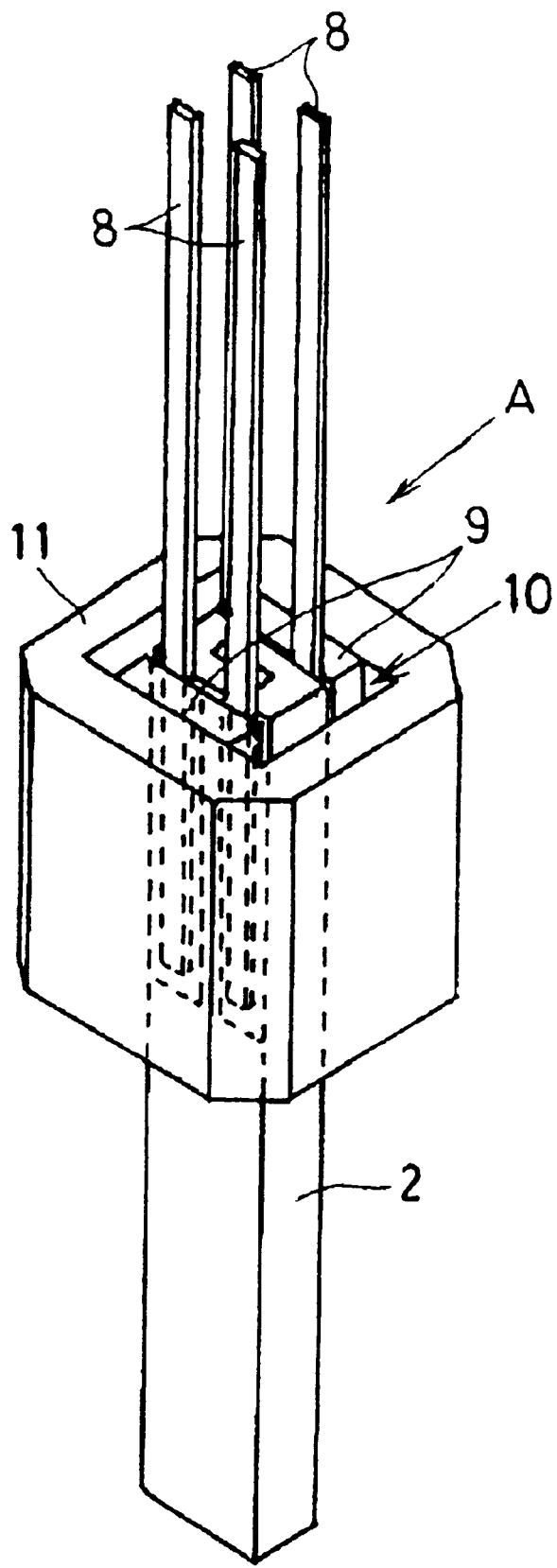
FIG. 3 is a perspective view showing the connection device of FIG. 1B.
Figures 4A, 4B, 4C:
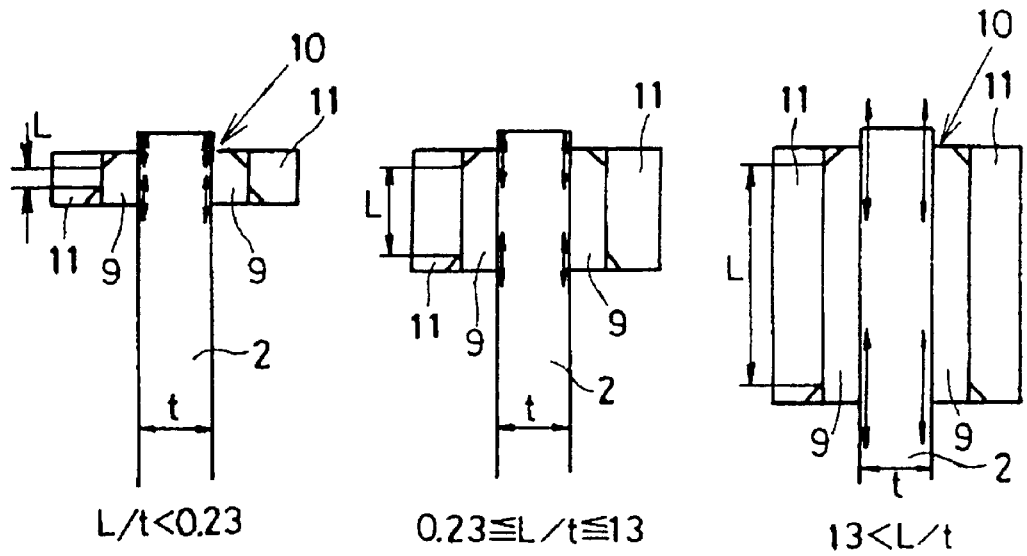
FIGS. 4A–4C are schematic views showing connection devices for a ceramic element used in experiments, wherein FIG. 4A corresponds to L/t<0.23, FIG. 4B corresponds to 0.23≦L/t≦13, and FIG. 4C corresponds to 13<L/t.
Figure 5:
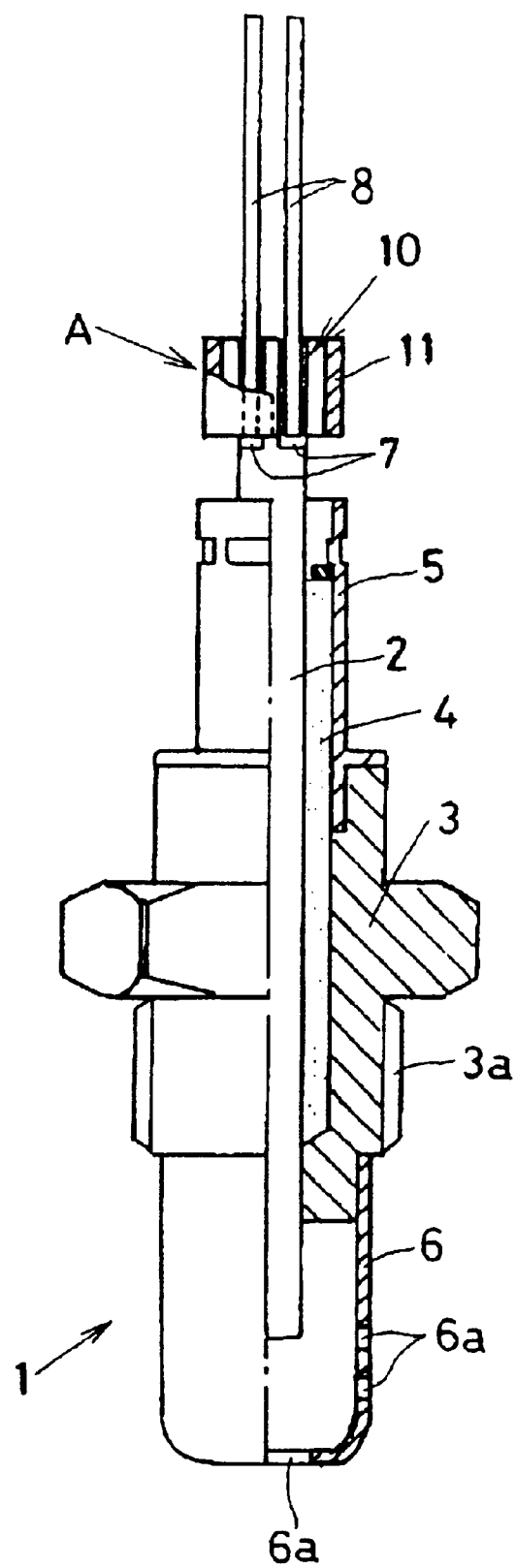
FIG. 5 is a sectional view showing related portions of an oxygen sensor.

FIGS. 1A through 5 are illustrations of one embodiment according to the present invention. Specifically, wherein FIGS. 1A–1B are sectional views illustrating a procedure for assembling a connection device A for a ceramic element, FIG. 2 is an enlarged sectional view showing related portions of the connection device A of FIG. 1, FIG. 3 is a perspective view of the connection device A of FIG. 1, FIGS. 4A–4C are schematic views of connection devices for a ceramic element used in experiments, and FIG. 5 is a sectional view showing related portions of an oxygen sensor using an oxygen sensor element, which is an example of a ceramic element.

As shown in FIG. 5, an oxygen sensor 1 includes a compact ceramic element 2. The ceramic element 2 may be, for example, an oxygen sensor element for determining an oxygen concentration within an exhaust pipe of a vehicle. The ceramic element 2 has a compact structure of a slender, rectangular parallelepiped in which an air-fuel ratio sensor portion and an electric heater portion are arranged in layers and sintered together. A tip portion of the ceramic element 2 is exposed to high-temperature exhaust gas flowing through the exhaust pipe. The ceramic element 2 is fixedly disposed within a cylindrical metallic fixture 3 by a glass seal 4 (or heat resistant cement) and a metallic retainer 5. The metallic fixture 3 is fixedly attached to the exhaust pipe by an attachment screw 3a such that a tip portion of the ceramic element 2 projects from a tip portion of the metallic fixture 3.

A metallic cover 6 is fixed to the tip portion of the metallic fixture 3 through resistance welding or similar process to cover the projected portion of the ceramic element 2. The cover 6 is formed as a cap having openings 6a formed therein for taking in high-temperature exhaust gas flowing through the exhaust pipe.

Two electrical connection portions 7 are metallized onto one side surface of a root portion of the ceramic element 2 for outputting a signal from the air-fuel ratio sensor portion. Also, two other electrical connection portions 7 are metallized onto the opposite side surface of the root portion of the ceramic element 2 in order to provide an electrical connection to the electrical heater portion. A lead strip 8 is electrically and mechanically connected to each electrical connection portion 7 of the ceramic element 2.

Since the oxygen sensor 1 is compact as described above, the entire oxygen sensor 1 reaches high temperatures due to the exposure to the exhaust heat. Accordingly, the electrical connection portions 7 of the ceramic element 2 and neighboring regions assume high working temperatures.

The joint structure resistant to high temperature according to one embodiment of the present invention will now be described.

As shown in FIGS. 1A through 3, an exemplary ceramic element 2 is formed as a slender, rectangular parallelepiped made of partially stabilized zirconia. The two electrical connection portions 7 are metallized onto each of the opposite side surfaces of the root portion of the ceramic element. Lead strips 8, formed of Inconel or stainless steel, for example, are placed on each of the electrical connection portions 7. The thus-assembled portion is held between two rectangular ceramic insulation sheets 9 of alumina, thereby forming an assembled body 10. A metallic ring member 11, formed of Incoloy or stainless steel, for example, having a rectangular tubular shape is interference-fitted onto the assembled body 10 using press fitting, hot-mode interference fitting, cold-mode interference fitting, or other appropriate process. Accordingly, in the assembled body, the insulation sheets 9 are fixedly interposed between the outer surfaces of the lead strips 8 and the ring element 11 with ease, thereby providing insulation between the lead strips and the ring member.

As shown in FIGS. 1A–1B, the ring member 11 has a retaining portion 11a whose inner dimension (i.e., retaining dimension) 'b' is smaller than an outer dimension (i.e., engaging dimension) 'a' of the assembled body 10 defined by a thickness of ceramic element 2 plus a total thickness of both lead strips 8 plus a total thickness of two insulation sheets 9. The assembled body 10 is retained within the retaining portion 11a by interference fitting. As shown in FIG. 2, the thickness t of the ceramic element 2 and the axial length L of the effective retaining portion of the ring member 11 are preferably determined within the relation 0.23≦L/t≦13.

In order to impart an appropriate joint strength on the lead strips 8, interference fitting between the assembled body 10 and the ring member 11 desirably has an interference amount (including an interference amount as measured after disassembly of the assembly of the assembled body 10 and the ring member 11) of at least 0.01 mm (i.e., 10 μm). When the interference amount is 10 μm or greater, an accompanying tensile stress is decreased, thereby obtaining a stable connection device without cracking the ceramic element.

An exemplary method of joining the ring member 11 onto the assembled body 10 through press fit will now be described with reference to FIGS. 1A–1B.

First, the press fit starting end of the retaining portion 11a of the ring member 11 is chamfered to form a chamfered portion 11b. The press fit starting end of the insulation sheet 9 is also chamfered to form a chamfered portion 9a. Then, the assembled body 10 including the ceramic element 2, four lead strips 8, and two insulation sheets 9 is held by a split-type jig 12a. Electrical connection portions 7 of the ceramic element 2 are retained by a jig 12b. Next, a lubricant (such as an emulsion of stearic acid) is applied onto the press fit starting end and press fit surface of the ring member 11. The ring member 11 is press-fitted onto the periphery of the assembled body 10. Before the press fit starting end of the ring member 11 reaches the split-type jig 12a, the split-type jig 12a is opened outward so that the ring member 11 is press-fitted onto the periphery of the assembled body 10. Then, the thus-press-fitted assembly may be heated to a temperature of 350° C. to decompose the lubricant, thereby increasing the retaining force exerted on the assembled body 10 by the ring member 11. Thus, the ring member 11 is press-fitted onto the periphery of the assembled body 10.

In the connection device for the ceramic element 2 of the oxygen sensor 1 used in a vehicle, the thickness t of the ceramic element 2 and the axial length L of the effective retaining apportion of the ring member 11 are preferably determined within the relationship $0.23 \leq L/t \leq 13$. As a result, even in a high-temperature atmosphere, tensile stress generated in the ceramic element 2 can be decreased, thereby preventing formation of cracks in a retained portion of the ceramic element 2. Thus, the ceramic element 2 remains a functional sensor.

Connection devices for ceramic elements according to the above-described embodiments of the present invention (hereinafter referred to as "examples") and connection devices for ceramic elements serving as comparative examples were subjected to one thousand cycles of a heat cycle fatigue test. Here, each cycle includes exposure to room temperature for twenty minutes. Afterwards, each ceramic element was evaluated to determine the degree of damage, if any.

The tested examples and comparative examples assumed the following specifications. Here, Incoloy 909 (trade name) is a heat resistant steel which contains Fe, Ni, and Cr. Inconel 750 (trade name) is a heat resistant steel which contains Ni as a main component, Fe, and Cr.

In the results of Table 1, the ring member 11 was made of Incoloy 909 having a minimum wall thickness of 0.7 mm and the length L of the effective retaining portion. Also, the ceramic element 2 was made of partially stabilized zirconia with a width of 4 mm and a thickness of 1.3 mm. The lead strip 8 is made of Inconel 750 with a width of 1.5 mm and a thickness of about 0.2 mm. The insulation sheet 9 was formed as a slender, rectangular parallelepiped made of alumina with a width of 4 mm and a thickness such that an interference amount was 0.01 mm. These elements were joined together through press fitting as illustrated in FIGS. 1A–1B. Some of the thus-obtained connection devices were disassembled to ensure that an effective interference amount is 0.01 mm. Test results are shown in Table 1.

TABLE 1

Experimental Example 1

| | t | L | L/t | Eval. | Test results |
|---|---|---|---|---|---|
| Comparative Example 1 | 1.311 | 0.20 | 0.153 | x | Major crack: Element function is disabled due to wire breaking |
| Comparative Example 2 | 1.305 | 0.25 | 0.192 | x | Major crack: Element function is disabled due to wire breaking |
| Example 1 | 1.297 | 0.30 | 0.231 | Δ | Minor crack: Element |
| Example 2 | 1.304 | 0.35 | 0.268 | ○ | No anomaly observed |
| Example 3 | 1.290 | 0.40 | 0.310 | ○ | No anomaly observed |
| Example 4 | 1.302 | 4.00 | 3.072 | ○ | No anomaly observed |
| Example 5 | 1.308 | 15.00 | 11.468 | ○ | No anomaly observed |
| Example 6 | 1.306 | 16.50 | 12.634 | ○ | No anomaly observed |

TABLE 1-continued

Experimental Example 1

| | t | L | L/t | Eval. | Test results |
|---|---|---|---|---|---|
| Example 7 | 1.313 | 17.00 | 12.947 | Δ | Minor crack: Element function is maintained |
| Comparative Example 3 | 1.296 | 17.50 | 13.503 | x | Major crack: Element function is disabled due to wire breaking |
| Comparative Example 4 | 1.311 | 18.00 | 13.730 | x | Major crack: Element function is disabled due to wire breaking |

Comparative Examples 1 and 2 correspond to FIG. 4A (i.e., L/t<0.23), Examples 1 through 7 correspond to FIG. 4B (i.e., $0.23 \leq L/t \leq 13$), and Comparative Examples 3 and 4 correspond to FIG. 4C (i.e., 13<L/t). As seen from Table 1, when the thickness t of the ceramic element 2 and the length L of the effective retaining portion of the ring member 11 satisfy the relation $0.23 \leq L/t \leq 13$, cracking of the ceramic element 2 is prevented during the thermal fatigue test. When the more preferable relation $0.26 \leq L/t \leq 12.7$ is satisfied, even minor cracks are not formed in the ceramic element 2.

Connection devices tested in Experimental Example 2 assumed structures similar to these of Experimental Example 1 except that the ceramic element 2 has a thickness 't' of 1.7 mm and that the ring member 11 has the thickness 'L' of the effective retaining portion as specified in Table 2. Test results are shown in Table 2. Here, even when the thickness t of the ceramic element 2 is increased to 1.7 mm, cracking of the ceramic element 2 is effectively prevented when the relation $0.23 L/t \leq 13$ is satisfied.

TABLE 2

Experimental Example 2

| | t | L | L/t | Eval. | Test results |
|---|---|---|---|---|---|
| Comparative Example 1 | 1.705 | 0.30 | 0.176 | x | Major crack: Element function is disabled due to wire breaking |
| Comparative Example 2 | 1.711 | 0.35 | 0.205 | x | Major crack: Element function is disabled due to wire breaking |
| Example 1 | 1.703 | 0.40 | 0.235 | Δ | Minor crack: Element function is maintained |
| Example 2 | 1.705 | 0.45 | 0.264 | ○ | No anomaly observed |
| Example 3 | 1.713 | 0.50 | 0.292 | ○ | No anomaly observed |
| Example 4 | 1.708 | 4.00 | 2.342 | ○ | No anomaly observed |
| Example 5 | 1.712 | 21.00 | 12.266 | ○ | No anomaly observed |
| Example 6 | 1.700 | 21.50 | 12.647 | ○ | No anomaly observed |
| Example 7 | 1.702 | 22.00 | 12.926 | Δ | Minor crack: Element function is maintained |
| Comparative Example 3 | 1.705 | 22.50 | 13.196 | x | Major crack: Element function is disabled due to wire breaking |
| Comparative Example 4 | 1.704 | 23.00 | 13.498 | x | Major crack: Element function is disabled due to wire breaking |

Connection devices tested in Experimental Example 3 assume structures similar to those of Experimental Example 1 except that the ceramic element 2 has a thickness t of 2.0 mm and that the ring member 11 has the thickness 'L' of the effective retaining portion as specified in Table 3. Test results are shown in Table 3. Here, even when the thickness t of the ceramic element 2 is increased to 2.0 mm, cracking of the ceramic element 2 is effectively prevented so long as the relation "$0.23 \leq L/t \leq 13$" is satisfied.

TABLE 3

Experimental Example 3

| | t | L | L/t | Eval. | Test results |
|---|---|---|---|---|---|
| Comparative Example 1 | 2.009 | 0.40 | 0.199 | x | Major crack: Element function is disabled due to wire breaking |
| Comparative Example 2 | 2.000 | 0.45 | 0.225 | x | Major crack: Element function is disabled due to wire breaking |
| Example 1 | 2.007 | 0.50 | 0.249 | Δ | Minor crack: Element function is maintained |
| Example 2 | 2.005 | 0.55 | 0.274 | o | No anomaly observed |
| Example 3 | 2.015 | 0.60 | 0.298 | o | No anomaly observed |
| Example 4 | 2.003 | 4.00 | 1.997 | o | No anomaly observed |
| Example 5 | 2.014 | 25.00 | 12.413 | o | No anomaly observed |
| Example 6 | 2.002 | 25.50 | 12.737 | o | No anomaly observed |
| Example 7 | 2.007 | 26.00 | 12.955 | Δ | Minor crack: Element function is maintained |
| Comparative Example 3 | 2.015 | 26.50 | 13.151 | x | Major crack: Element function is disabled due to wire breaking |
| Comparative Example 4 | 2.017 | 27.00 | 13.386 | x | Major crack: Element function is disabled due to wire breaking |

TABLE 4

Experimental Example 4

| | t | L | L/t | Eval. | Test results |
|---|---|---|---|---|---|
| Comparative Example 1 | 1.803 | 0.40 | 0.222 | x | Major crack: Element function is disabled due to wire breaking |
| Comparative Example 2 | 1.794 | 0.50 | 0.279 | x | Major crack: Element function is disabled due to wire breaking |
| Example 1 | 1.801 | 0.55 | 0.305 | Δ | Minor crack: Element function is maintained |
| Example 2 | 1.812 | 0.60 | 0.331 | o | No anomaly observed |
| Example 3 | 1.793 | 0.65 | 0.363 | o | No anomaly observed |
| Example 4 | 1.807 | 4.00 | 2.214 | o | No anomaly observed |
| Example 5 | 1.782 | 14.00 | 7.856 | o | No anomaly observed |
| Example 6 | 1.812 | 14.50 | 8.002 | o | No anomaly observed |
| Example 7 | 1.801 | 15.00 | 8.329 | Δ | Minor crack: Element function is maintained |
| Comparative Example 3 | 1.799 | 15.50 | 8.616 | x | Major crack: Element function is disabled due to wire breaking |
| Comparative Example 4 | 1.804 | 16.00 | 8.869 | x | Major crack: Element function is disabled due to wire breaking |

Figure 6:
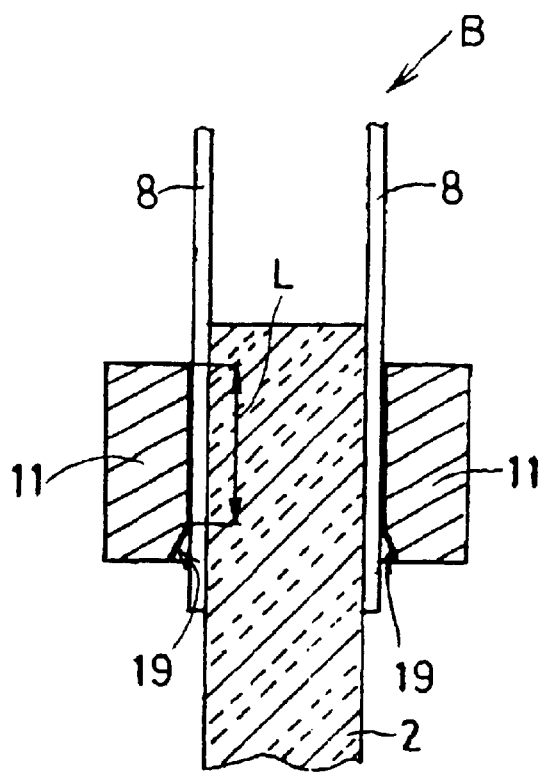
FIG. 6 is a sectional view showing related portions of a connection device for a ceramic element according to another embodiment of the present invention.
Figure 7:
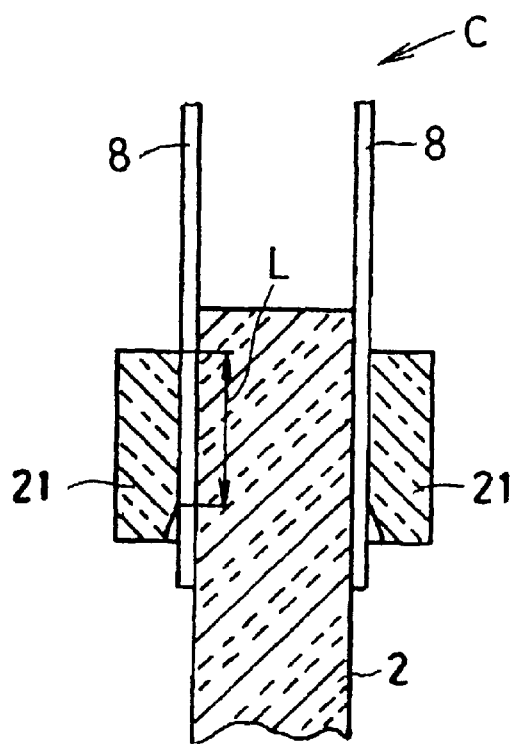
FIG. 7 is a sectional view showing related portions of a connection device for a ceramic element according to a further embodiment of the present invention.

FIGS. 6 and 7 illustrate connection devices according to additional embodiments of the present invention.

As shown in FIG. 6, in a connection device B for the ceramic element 2, an insulation layer 19 is integrally formed on at least a portion of the inner surface of the ring member 11 to face the outer surfaces of the lead strips 8. Employment of the insulation layer 19 enables reduction in thickness of the insulation sheet used for insulation of the lead strips 8, thereby making the connection device B more compact and imparting excellent impact resistance thereto.

As shown in FIG. 7, in a connection device C for the ceramic element shown in FIG. 7, the ring member 21 is made of an insulating material (for example, resin or ceramic). As a result, the connection device C is also made compact, thereby yielding similar advantages as those of the connection device B of FIG. 6.

Connection devices whose ring members 11 were made of Waspaloy (trade name) were manufactured. Waspaloy is an ultra heat resistant alloy which contains nickel as a major component. The ring member 11 had a minimum wall thickness of 0.7 mm and the length L of the effective retaining portion as specified in Table 4 (Experimental Example 4). The ceramic element 2 was formed of partially stabilized zirconia with a width of 3 mm and a thickness of 1.8 mm. The lead strip 8 was made of Inconel 750 with a width of 1 mm and a thickness of about 0.2 mm. The insulation sheet 9 was formed of alumina as a slender, rectangular parallelepiped with a width of 3 mm and a thickness such that an interference amount was 0.01 mm. These elements were joined together through press fitting as illustrated in FIGS. 1A–1B. The thus-obtained connection devices were subjected to a heat cycle fatigue test under conditions similar to those of Experimental Example 1. Test results are shown in Table 4. The trial-manufactured connection devices were disassembled to ensure that an effective interference amount was 0.01 mm.

TABLE 5

Experimental Example 5

| | t | L | L/t | Eval. | Test results |
|---|---|---|---|---|---|
| Comparative Example 1 | 1.802 | 0.50 | 0.277 | x | Major crack: Element function is disabled due to wire breaking |
| Comparative Example 2 | 1.799 | 0.55 | 0.306 | x | Major crack: Element function is disabled due to wire breaking |
| Example 1 | 1.802 | 0.60 | 0.333 | Δ | Minor crack: Element function is maintained |
| Example 2 | 1.807 | 0.65 | 0.360 | o | No anomaly observed |
| Example 3 | 1.791 | 0.70 | 0.391 | o | No anomaly observed |
| Example 4 | 1.796 | 4.00 | 2.227 | o | No anomaly observed |
| Example 5 | 1.793 | 11.00 | 6.135 | o | No anomaly observed |
| Example 6 | 1.811 | 11.50 | 6.350 | o | No anomaly observed |
| Example 7 | 1.799 | 12.00 | 6.670 | Δ | Minor crack: Element function is maintained |
| Comparative Example 3 | 1.811 | 12.50 | 6.902 | x | Major crack: Element function is disabled due to wire breaking |
| Comparative Example 4 | 1.814 | 13.00 | 7.166 | x | Major crack: Element function is disabled due to wire breaking |

Figure 8:
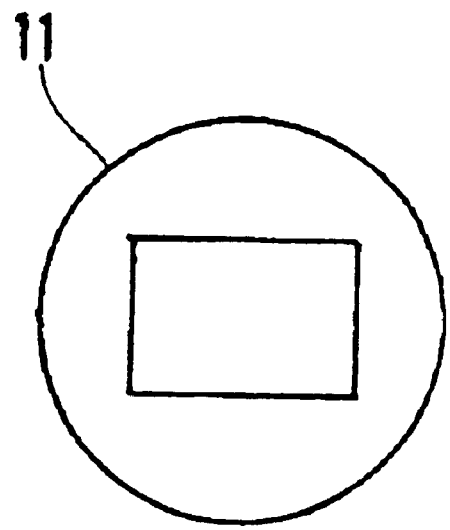
FIG. 8 is a plan view showing a modified example of a ring member.
Figure 9:
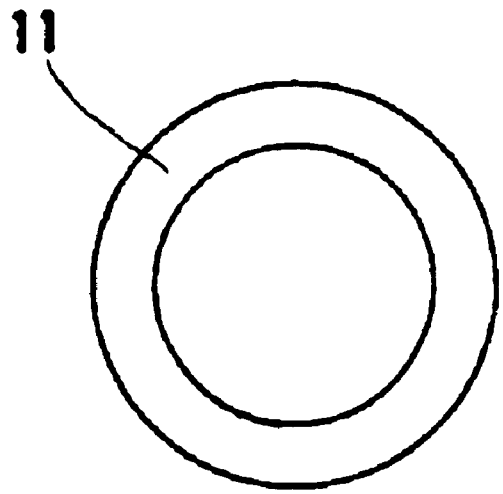
FIG. 9 is a plan view showing another modified example of a ring member.
Figure 10:
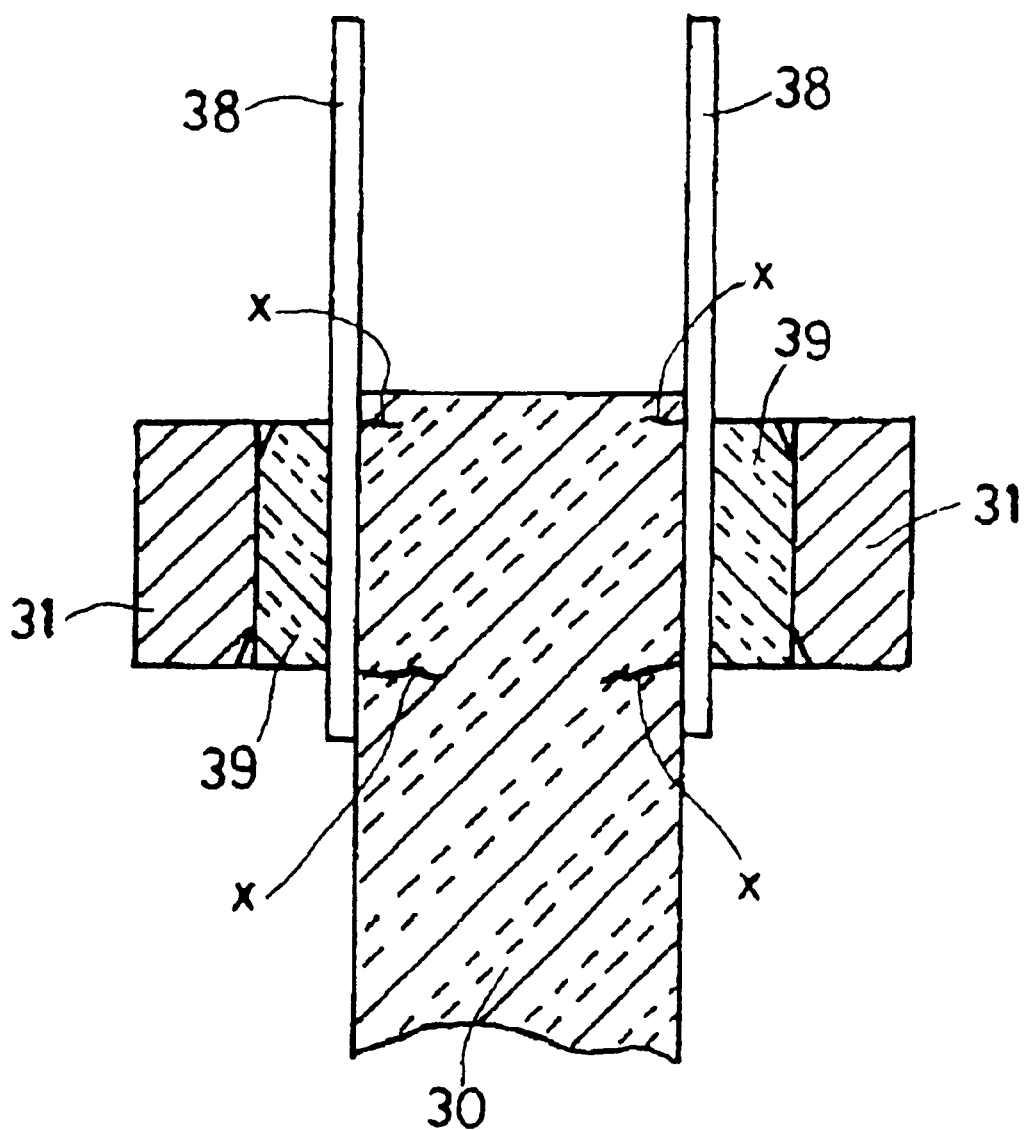
FIG. 10 is a sectional view illustrating formation of cracks in a ceramic element of a connection device.

While the foregoing description has described specific exemplary configurations of the present invention, other configurations may be selected as desired. For example, the above embodiments have been described with the shape of the ring member 11 having a rectangular tubular form. However, a peripheral shape may be cylindrical as shown in FIG. 8, or both the peripheral shape and a hole shape may be cylindrical as shown in FIG. 9. When the ring member 11 has a cylindrical hole formed therein, the periphery of he insulation sheet 9 may be formed into an arcuate shape. Of course, other appropriate variants may also be selected.

Similarly, the above embodiments are described wherein the ceramic element 2 is an oxygen sensor element used in an oxygen sensor 1. However, the ceramic element 2 may be used with any other type gas sensor element, such as an NOx sensor element, a CO sensor element, or a $CO_2$ sensor element.

In accordance with the present invention, a connection device is provided to prevent cracking of the ceramic element, thereby reliably maintaining sensor function. The thickness t of the ceramic element and the axial length L of an effective retaining portion of the ring member satisfy the relation "$0.23 \leq L/t \leq 13$." Here, the effective retaining portion L of the ring member is measured as the effective longitudinal length of a contact surface between the inner surface of the ring member and the outer surface of the ceramic element excluding the chamfered portion formed at the inner end surface of the ring member and the chamfered portion formed at the outer end surface of the ceramic element. Preferably, the thickness t of the ceramic element and the axial length L of the effective retaining portion of the ring member satisfy the relation "$0.26 \leq L/t \leq 12.7$."

When $0.23 \leq L/t \leq 13$, as shown in FIG. 4B, even though a tensile stress exerted at each axial fitting end is relatively large, the tensile stresses exerted at the axially opposite fitting ends do not interfere with each other. Instead, the tensile stresses act independently of each other since the distance between the axially opposite fitting ends is relatively long.

When $L/t<0.23$, as shown in FIG. 4A, the stress exerted at each fitting end becomes small. However, since the axially opposite fitting ends are close to each other, the stresses exerted at the axially opposite fitting ends overlap each other, thereby resulting in relatively large composite stress. As a result, cracks are formed in the sensor element, thereby causing the wire to break at a lead portion that connects the sensing portion with the electrical connection portion. Thus, the sensor element fails to function properly.

When $13<L/t$, as shown in FIG. 4C, the stresses exerted at the axially opposite fitting ends are independent of each other, but are excessively large, thereby causing cracks to form in the ceramic element.

It will be apparent to those skilled in the art that various modifications and variations can be made in the connection device for ceramic element of the present invention without departing from the spirit or scope of the invention. Thus, it is intended that the present invention cover the modifications and variations of this invention provided they come within the scope of the appended claims and their equivalents.

What is claimed is:

1. A connection device for a ceramic gas sensor element, comprising:
    a sensor assembly including a ceramic element having a thickness t, an electrical connection portion formed on a side of the ceramic element, and at least one electrical lead in contact with the electrical connection portion, the sensor assembly defining an outer dimension at a position corresponding to the electrical connection portion;
    a ring member for holding the at least one electrical lead in contact with the electrical connection portion, the ring member being disposed around the sensor assembly and having an inner dimension at a position corresponding to the electrical connection portion that is smaller than the outer dimension of the sensor assembly, the ring member having an axial length L in contact with the sensor assembly,
    wherein the thickness t and the axial length L satisfy the relationship $0.23 \leq L/t \leq 13$.

2. The connection device for a ceramic gas sensor element according to claim 1, wherein the sensor assembly further includes an insulation sheet interposed at least between the at least one electrical lead and the ring member.

3. The connection device for a ceramic gas sensor element according to claim 1, wherein the ring member includes an insulation layer integrally formed on at least a portion of an inner surface of the ring member to face the at least one electrical lead.

4. The connection device for a ceramic gas sensor element according to claim 1, wherein the ring member is formed of an insulating material, the ring member being directly in contact with the at least one electrical lead.

5. The connection device for a ceramic gas sensor element according to claim 1, wherein the sensor assembly further includes one of an oxygen sensor element, an NOx sensor element, a CO sensor element, and a $CO_2$ sensor element.

6. The connection device for a ceramic gas sensor element according to claim 1, wherein the ring member is interference-fitted onto the sensor assembly.

7. The connection device for a ceramic gas sensor element according to claim 1, wherein the ceramic element has substantially rectangular tubular form.

8. The connection device for a ceramic gas sensor element according to claim 7, wherein the ring member has a substantially rectangular hole.

9. The connection device for a ceramic gas sensor element according to claim 1, wherein the ceramic element is substantially a rectangular parallelepiped.

10. The connection device for a ceramic gas sensor element according to claim 9, wherein the ring member has a substantially rectangular hole.

11. The connection device for a ceramic gas sensor element according to claim 1, wherein the ceramic element is substantially cylindrical.

12. The connection device for a ceramic gas sensor element according to claim 11, wherein the ring member has a substantially circular hole.

13. The connection device for a ceramic gas sensor element according to claim 1, wherein an inner surface of the ring member has a chamfered portion, the axial length L excluding the chamfered portion.

14. The connection device for a ceramic gas sensor element according to claim 1, wherein the thickness t and the axial length L satisfy the relation $0.26 \leq L/t \leq 12.7$.

15. A connection device for a ceramic gas sensor element, comprising:
    an assembled body including a ceramic element having an electrical connection portion and lead strips in contact with the electrical connection portion and extending outward; and
    a ring member having an inner dimension smaller than an outer dimension of the assembled body, the ring member being interference-fitted onto the assembled body to thereby mechanically press the lead strips against the electrical connection portion of the ceramic element,
    wherein a thickness t of the ceramic element and an axial length L of a portion of the ring member in contact with the assembled body satisfy the relationship $0.23 \leq L/t \leq 13$.

16. The connection device for a ceramic gas sensor element according to claim 15, wherein the assembled body further includes an insulation sheet interposed at least between outer surfaces of the lead strips and the ring member.

17. The connection device for a ceramic gas sensor element according to claim 15, wherein an insulation layer is integrally formed on at least a portion of an inner surface of the ring member that faces the outer surfaces of the lead strips.

18. The connection device for a ceramic gas sensor element according to claim 15, wherein the ring member is made of an insulating material, and the ring member directly contacts the lead strips.

19. The connection device for a ceramic gas sensor element according to claim 15, wherein the assembled body includes one of an oxygen sensor element, an NOx sensor element, a CO sensor element, and a $CO_2$ sensor element.

20. A connection device for a ceramic gas sensor element, comprising:

a ceramic element having a thickness t;

an electrical connection portion formed on a side of the ceramic element;

an electrical lead in contact with the electrical connection portion;

an insulating layer disposed on the electrical lead; and a ring member disposed around the ceramic element, the electrical connection portion, the electrical lead, and the insulating layer to hold the electrical lead in contact with the electrical connection portion, wherein the ring member has an inner dimension that is smaller than an outer dimension defined by the ceramic element, the electrical connection portion, the electrical lead, and the insulating layer, and wherein the ring member has an axial length L in contact with the insulating layer such that the thickness t and the axial length L satisfy the relationship $0.23 \leq L/t \geq 13$.

* * * * *